US00PP37775P2

(12) United States Plant Patent
Macgregor et al.

(10) Patent No.: US PP37,775 P2
(45) Date of Patent: Oct. 13, 2026

(54) ***HESPERANTHA* PLANT NAMED 'MACHESPIBU'**

(50) Latin Name: ***Hesperantha* hybrid**
Varietal Denomination: MACHESPIBU

(71) Applicants: Elizabeth Macgregor, Kirkcudbright (GB); Alasdair John Macgregor, Kirkcudbright (GB)

(72) Inventors: Elizabeth Macgregor, Kirkcudbright (GB); Alasdair John Macgregor, Kirkcudbright (GB)

(73) Assignee: Elizabeth MacGregor's Nursery, Kirkcudbright (GB)

( * ) Notice: Subject to any disclaimer, the term of this patent is extended or adjusted under 35 U.S.C. 154(b) by 0 days.

(21) Appl. No.: 19/651,722

(22) Filed: Apr. 19, 2026

(51) Int. Cl.
*A01H 6/00* (2018.01)
*A01H 5/02* (2018.01)

(52) U.S. Cl.
USPC ..... Plt./263.1

(58) Field of Classification Search
USPC ..... Plt./263.1
See application file for complete search history.

*Primary Examiner* — Karen M Redden
(74) *Attorney, Agent, or Firm* — James R. Holm; Plant Novelty Rights, LLC

(57) ABSTRACT

A new and distinct *Hesperantha* plant named 'MACHESPIBU' particularly distinguished by: a very floriferous habit, producing a high number of flowers per plant; a vibrant, bright and clear pink flower color; a late flowering season, typically beginning in early September and continuing into autumn under UK and Dutch growing conditions; and an upright and tall plant habit with strong flowering stems.

3 Drawing Sheets

Figure 1:
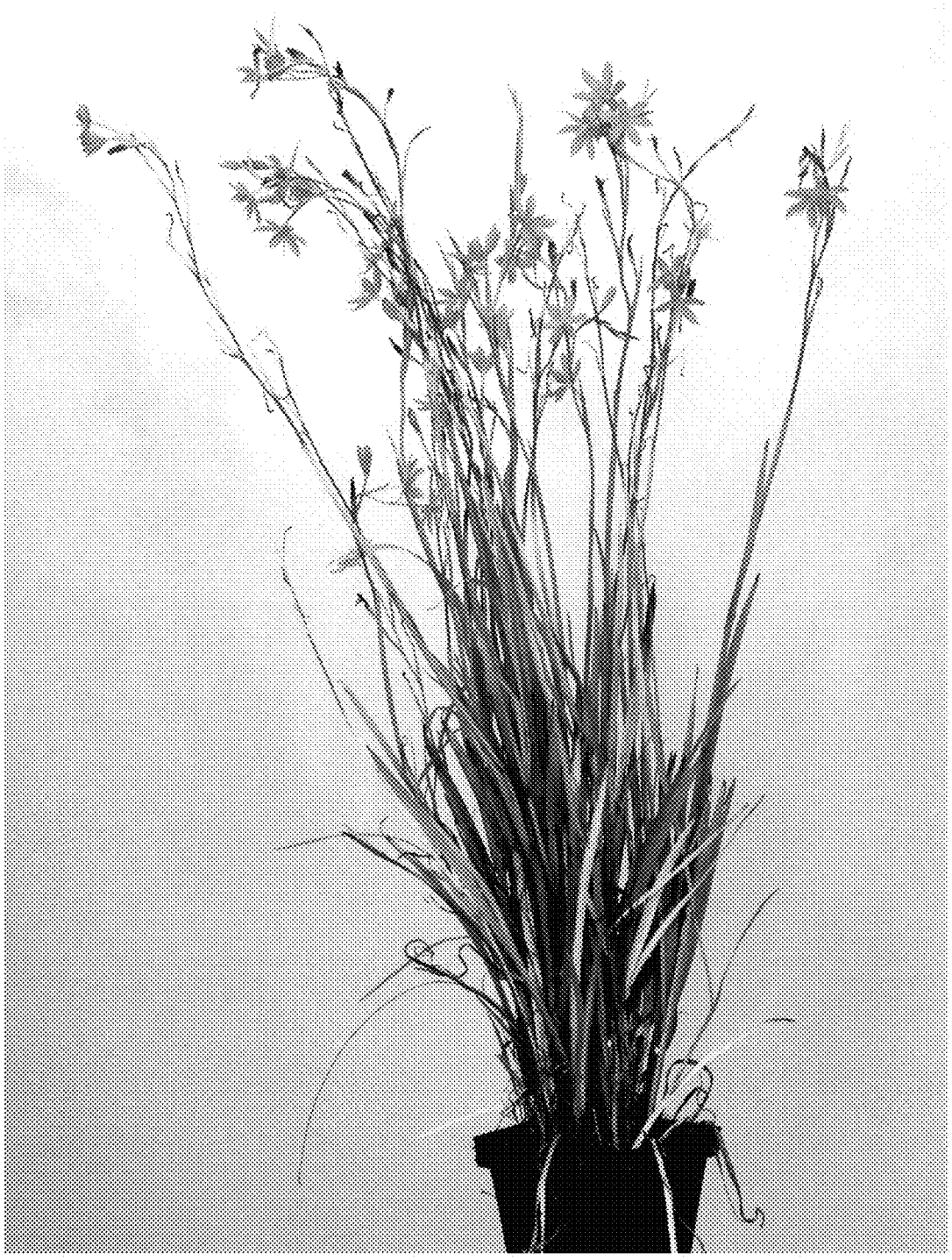

Genus and species: *Hesperantha* hybrid.
Variety denomination: 'MACHESPIBU'.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosures and/or sales that fall within a one-year grace period prior to the filing date.

BACKGROUND OF THE NEW PLANT

The present invention comprises a new and distinct variety of *Hesperantha* plant, botanically known as *Hesperantha* hybrid and hereinafter referred to by the variety name 'MACHESPIBU'. The new *Hesperantha* variety 'MACHESPIBU' is the result of a controlled cross-pollination breeding program carried out by the inventors in a commercial nursery located in Kirkcudbright, Scotland in 2017. The inventors performed the controlled cross-pollination between *Hesperantha coccinea* 'White Admiral' (unpatented), as the seed parent, with an unnamed and unpatented *Hesperantha huttonii* plant as the pollen parent. Seed from said cross was harvested, then germinated, and the resulting seedlings were grown to a mature, flowering size. In 2020, the inventors selected the new *Hesperantha* cultivar 'MACHESPIBU' as a single unique plant from amongst the progeny from said cross due to its novel ornamental characteristics including a floriferous habit, vibrant and clear pink flower color, and late flowering season. This new and distinctive *Hesperantha* cultivar was given the name 'MACHESPIBU'.

The new *Hesperantha* cultivar 'MACHESPIBU' was first reproduced asexually in 2020 by meristematic tissue culture at a laboratory in Heerhugowaard, the Netherlands. Asexual propagation by meristematic tissue culture and by underground cormels has shown that the unique features of the new cultivar are stable and reproduced true-to-type to date through seven successive generations.

SUMMARY OF THE INVENTION

The new *Hesperantha* cultivar 'MACHESPIBU' has not been observed under all possible environmental conditions. The phenotype may vary somewhat with variations in environment such as temperature, day length, light intensity, water status, fertilizer rate and type, without, however, any variance in genotype.

The following are the most outstanding and distinguishing characteristics of this new cultivar. The combination of these characteristics distinguishes 'MACHESPIBU' as a new and distinct variety of *Hesperantha*.

1. *Hesperantha* 'MACHESPIBU' exhibits a very floriferous habit, producing a high number of flowers per plant.
2. *Hesperantha* 'MACHESPIBU' exhibits a vibrant, bright and clear pink flower color.
3. *Hesperantha* 'MACHESPIBU' exhibits a late flowering season, typically beginning in early September and continuing into autumn under UK and Dutch growing conditions.
4. *Hesperantha* 'MACHESPIBU' exhibits an upright and tall plant habit with strong flowering stems.

DESCRIPTION OF THE PHOTOGRAPHS

This new *Hesperantha* cultivar is illustrated by the accompanying-colored photographs which show the overall appearance and distinct characteristics of the plant. The colors shown are as true as can be reasonably obtained by conventional photographic procedures. The photographs are of 26-week-old plants grown in-ground in an outdoor nursery in Kirkcudbright, Scotland. Plants were subsequently potted into 14-centimeter circular containers to ascertain the botanical characteristics. Colors in the photographs may differ slightly from the color values cited in the botanical description which accurately describes the colors of the new variety.

FIG. 1. shows the overall plant form, foliage, and inflorescence of 'MACHESPIBU'.

Figure 2:
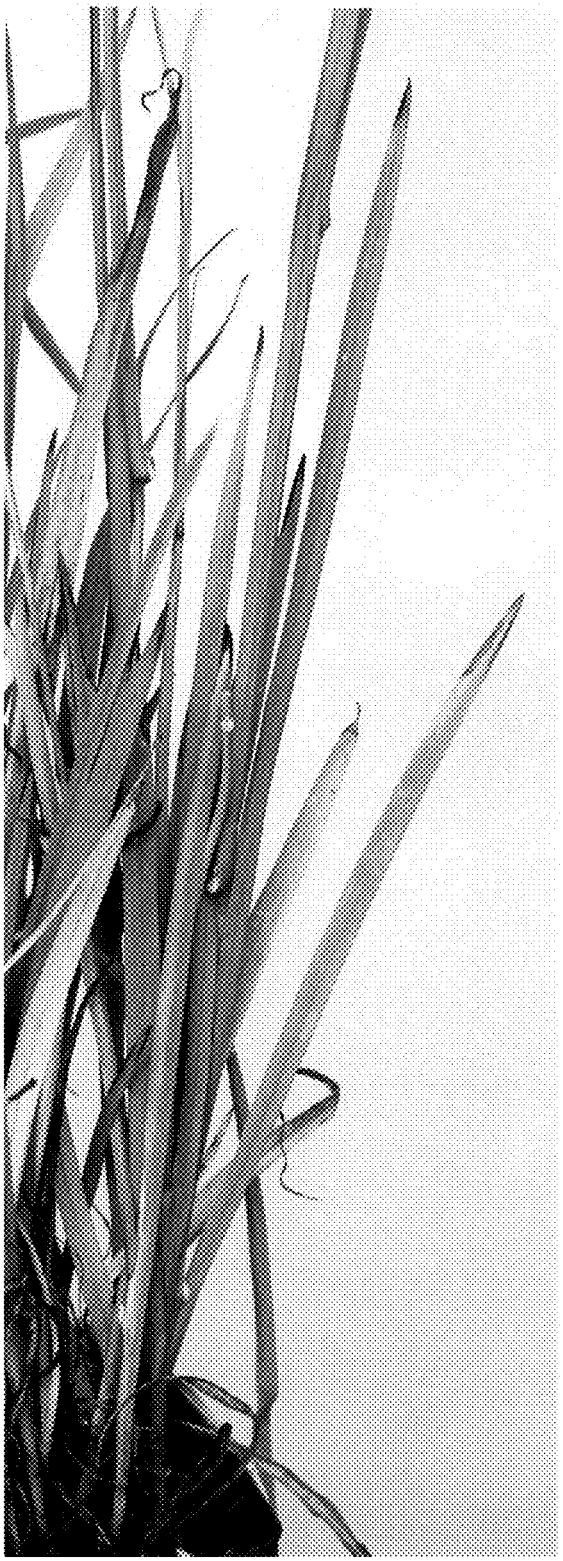

FIG. 2. shows a close-up of typical foliage of 'MACHESPIBU'.

Figure 3:
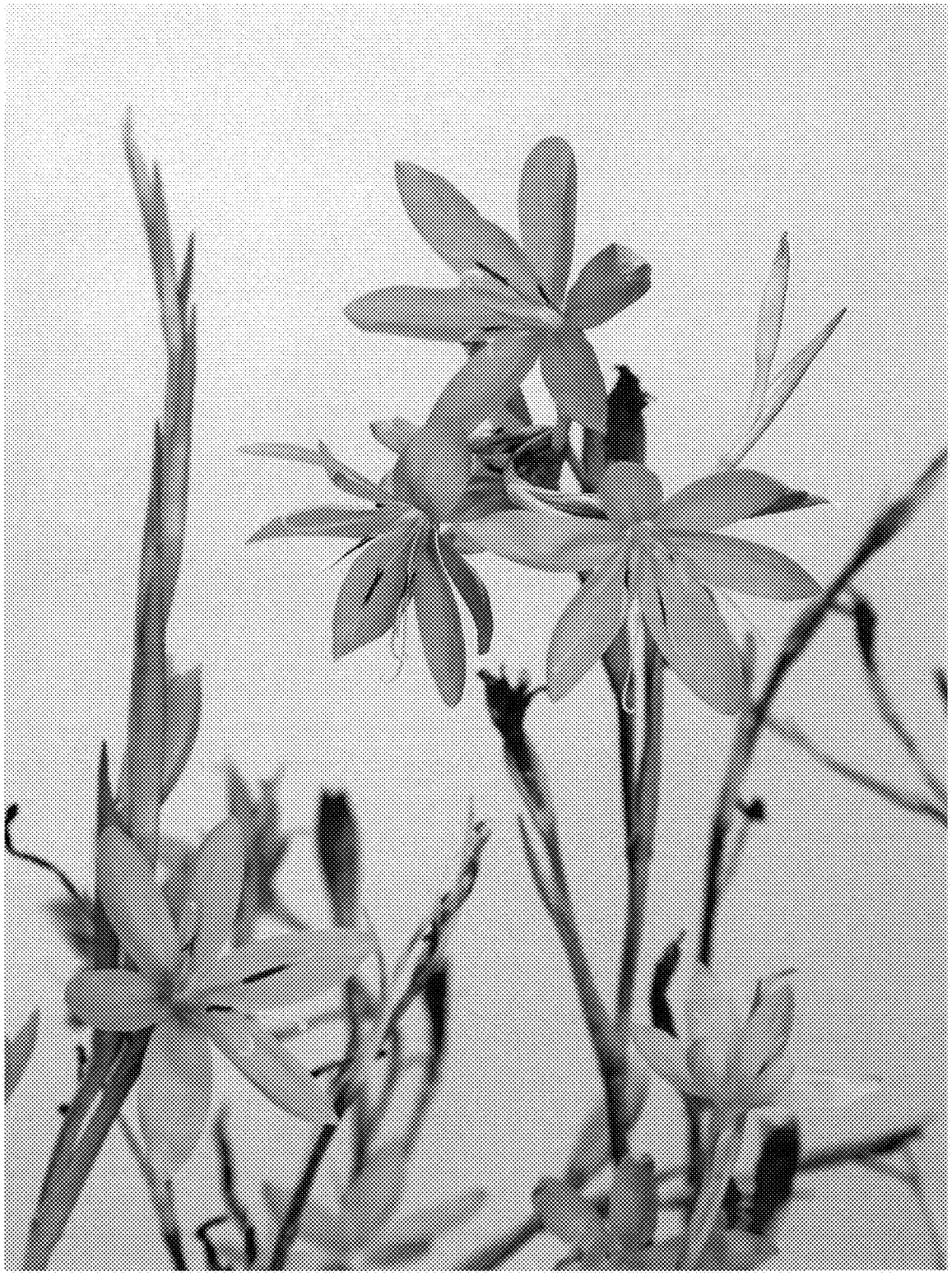

FIG. 3. shows a close-up of typical flowers of 'MACHESPIBU'.

DESCRIPTION OF THE NEW VARIETY

In the following description, color references are made to The Royal Horticultural Society Colour Chart, Sixth Edition, except where general color terms of ordinary dictionary significance are used.

The following observations and measurements describe plants grown in an outdoor nursery located in Kirkcudbright, Scotland. Plants were grown in-ground under normal light levels with no supplemental light. Average daytime temperatures ranged from +20° C. to +25° C. and average nighttime temperatures ranged from +10° C. to +15° C. Detailed descriptions were taken in October 2025 from 26-week-old field grown plants subsequently potted into 14-centimeter circular containers. Measurements and numerical values represent averages of typical plant types.

DETAILED BOTANICAL DESCRIPTION

Classification:

*Family*.—Iridaceae.

*Botanical*.—*Hesperantha* hybrid.

*Denomination*.—'MACHESPIBU'.

General description:

*Plant type*.—Herbaceous perennial.

*Crop time*.—Approximately 20 to 24 weeks from propagation to a saleable flowering plant.

*Growth habit*.—Upright with flowering stems emerging from the base of the plant.

*Height from soil level to top of foliar plane*.—Average 55.4 cm.

*Height from soil level to top of floral plane*.—Average 82.3 cm.

*Plant diameter or area of spread*.—Average 49.5 cm.

*Plant vigor*.—Moderate.

*Growth rate*.—Moderate.

*Cormel description*.—Shape: Ovate to near globular. Length: Average 0.6 cm. Diameter: 0.55 cm. Texture: Slightly glossy, smooth and glabrous. Color: White, 155A and strongly tinged greyed-purple, 184C.

Stems:

*Branching habit*.—Basally branched with main flowering stems emerging from the base of the plant, no lateral branching.

*Number of primary (main) stems per plant*.—Average 31.

*Shape and texture*.—Rounded, smooth and glabrous.

*Luster*.—Moderately glossy.

*Length*.—Average 63.6 cm from the base of the plant to the lowest flower.

*Diameter*.—Average 0.35 cm.

*Internode length*.—Average 17.4 cm.

*Attitude*.—Average angle of 10 degrees from vertical.

*Strength*.—Strong.

*Color*.—Juvenile stems: Yellow-green, 144A and covered with a very thin greyed-green waxy layer, 193B. Mature stems: Yellow-green, 144C and covered with a very thin greyed-green waxy layer, 193B. At internodes: Yellow-green, 146B.

*Pubescence*.—None.

Foliage description:

*General*.—Flat, sessile and sheathing leaves which are typically axially folded with the edges fused together, only the undersides are visible.

*Division*.—Simple.

*Arrangement*.—Alternate, equitant.

*Number of leaves per flowering stem*.—Average 5.

*Leaf shape*.—Linear.

*Leaf aspect*.—Flat, typically folded with edges fused.

*Leaf length*.—Average 30.1 cm.

*Leaf width*.—Average 0.8 cm.

*Leaf apex*.—Narrow acuminate.

*Leaf base*.—Sheathing.

*Sheath*.—Length: Average 9.0 cm. Width: Average 0.4 cm. Color: Yellow-green, 146B and fading to 146D at the base, tinged greyed- orange, 175C.

*Leaf margin*.—Entire.

*Leaf texture, upper and lower surfaces*.—Smooth and glabrous.

*Leaf pubescence*.—Not present.

*Leaf rugosity*.—Non-rugose.

*Leaf luster*.—Upper surface: Glossy. Lower surface: Matte.

*Juvenile leaf color*.—Upper surface: Yellow-green, 145B. Lower surface: Yellow-green, 144B.

*Mature leaf color*.—Upper surface: Greyed-green, 194A and 194B. Lower surface: Green, 137B.

*Leaf venation*.—Pattern: Parallel. Color, upper surface: Green, NN137B. Color, lower surface: Green, 138A.

Inflorescence description:

*Type*.—Spike.

*Natural flowering season*.—Late summer.

*Time to flower*.—Approximately 20 to 24 weeks from propagation.

*Height*.—Average 25.4 cm.

*Diameter*.—Average 8.0 cm.

*Quantity of flowers per inflorescence*.—Average 10.

*Quantity of flowers per plant*.—Average 260.

*Quantity of flower buds per plant*.—Average 50.

*Quantity of flowers and flower buds per plant*.—Average 310.

*Peduncles*.—Terminal peduncle length: Average 21.5 cm. Terminal peduncle diameter: Average 0.225 cm. Orientation: Upright, vertical. Strength: Strong. Texture: Smooth and glabrous. Luster: Slightly glossy. Color: Yellow-green, a blend of 144A and 144B and covered with a very thin greyed-green waxy layer, 193B.

Flower buds:

*Shape*.—Oblanceolate.

*Length*.—3.5 cm.

*Diameter*.—0.4 cm.

*Texture*.—Smooth and glabrous.

*Luster*.—Slightly glossy.

*Color*.—Red-purple, 68B with a yellow-green tube, 153D.

Flower:

*General*.—Perianth consisting of two whorls of sessile tepals, identical in shape, size and color; the lower whorl is approximately 52.5 percent fused.

*Type*.—Single, tubular shaped flower.

*Habit*.—Freely flowering.

*Orientation*.—Outwardly to slantly drooping and slantly upright.

*Longevity*.—2 to 3 days.

*Persistent or self-cleaning*.—Self-cleaning.

*Fragrance*.—Non fragrant.

*Horizontal diameter*.—Average 4.5 cm.

*Vertical diameter*.—Average 4.5 cm.

*Depth*.—Average 6.5 cm.

*Throat*.—Diameter: Average 0.3 cm. Texture: Smooth and glabrous. Color: Yellow-green, 145A and 145B.

*Tube*.—Length: Average 3.3 cm. Diameter: 0.15 cm. Texture: Smooth and glabrous. Color: Yellow-green, 150C and moderately to strongly tinged greyed-orange, 174D.

*Tepals*.—Arrangement: Rotate. Quantity per flower: Average of 6. Shape: Obovate, slightly to moderately convex. Length: Average 3.0 cm, excluding tube. Diameter: Average 1.1 cm. Apex: Acute. Base: Cuneate, fused. Margin: Entire. Texture, upper and lower surfaces: Smooth and glabrous. Rugosity, upper and lower surfaces: Non-rugose. Luster, upper and lower surfaces: Very slightly glossy. Color, when opening: Upper surface: Red-purple, a blend of 68A and 68B. Lower surface: Red-purple, 67C. Color, when fully opened: Upper surface: Red-purple, 68A. Lower surface: Red-purple, a blend of 67C and 67D. Color, when fading: Upper surface: Red-purple, 64C. Lower surface: Red-purple, 64C.

*Bracts*.—General: Two floral bracts present at the base of each flower, alternately spaced and folded around the flower tube; the lower bract larger than the upper bract. Shape, upper and lower bract: Lanceolate with a narrow acuminate apex and cuneate base. Lower bract length: Average 4.6 cm. Upper bract length: Average 3.4 cm. Lower bract width: Average 0.8 cm. Upper bract width: Average 0.5 cm. Texture, upper and lower bract: Smooth and glabrous. Luster, upper and lower bract: Matte. Color, upper and lower bract: Upper surface: Yellow-green: 144B and veined green, 143B. Lower surface: Yellow-green: 144A.

Reproductive organs:

*Stamens*.—Quantity per flower: Average 3. Anthers: Shape: Basifixed, narrow oblong. Length: Average 1.0 cm. Width: Average 0.75 mm. Color: Yellow, 13C and fading grey-brown when maturing, N199C. Filaments: Length: Average 1.2 cm. Color: Red-purple, 68B and fading yellow-green towards the flower tube, 145A and 145B. Pollen: Amount: Low. Color: Yellow-orange, 22A.

*Pistil*.—Quantity per flower: 1. Length: Average 5.3 cm. Style: Length: Average 2.3 cm. Color: Yellow-green, 145D. Stigma: Shape: Cleft, three parted and curled. Length: Average 3.0 cm. Diameter: Average 0.1 cm. Color: Red-purple, 68B. Ovary color: Yellow-green, 144B and fading a lighter yellow-green towards the base, 144C.

Seed and fruit: Non observed to date.

USDA hardiness zones: 8 to 11.

Hight temperature tolerance: At least tolerant to temperatures up to 40 degrees Celsius.

Low temperature tolerance: At least tolerant to temperatures down to minus 9 degrees Celsius.

Rain tolerance: Moderate.

Wind tolerance: Low.

Disease and pest tolerance: No claims are made to any superior disease or insect resistance or tolerance.

COMPARISON WITH THE PARENT PLANTS

The new *Hesperantha* cultivar 'MACHESPIBU' can be distinguished from its seed parent *Hesperantha* 'White Admiral' (unpatented) in the following characteristics described in Table 1 below.

TABLE 1

| Characteristic | 'MACHESPIBU' | 'White Admiral' |
|---|---|---|
| Flower color. | Bright, clear pink. | White. |
| Flower intensity. | Vivid and saturated. | Soft and subdued. |
| Floriferousness. | Very floriferous and dense. | Moderately floriferous and less dense. |
| Flowering season. | Late, from early September. | Earlier. |
| Plant habit. | Upright and dense. | Less upright and more open. |

The new *Hesperantha* cultivar 'MACHESPIBU' can be distinguished from its unnamed and unpatented pollen parent *Hesperantha huttonii* in the following characteristics described in Table 2 below.

TABLE 2

| Characteristic | 'MACHESPIBU' | *Hesperantha huttonii* |
|---|---|---|
| Flower color. | Bright, clear pink. | Lighter colored and less vivid pink. |
| Floriferousness. | Very floriferous and dense. | Less floriferous, more open and less dense. |
| Plant habit. | Upright, dense and uniform. | More open and less uniform. |
| Plant height. | Taller. | Shorter. |

COMPARISON WITH RELATED KNOWN VARIETY

The new *Hesperantha* cultivar 'MACHESPIBU' can be distinguished from the related known variety of *Hesperantha* 'Elburton Glow' (unpatented) in the following characteristics described in Table 3 below.

TABLE 3

| Characteristic | 'MACHESPIBU' | 'Elburton Glow' |
|---|---|---|
| Flower color. | Bright, clear pink. | Salmon-pink with orange undertones. |
| Color clarity. | Clean and vivid | Slightly muted with warmer tones. |
| Floriferousness. | Very floriferous and dense. | Less floriferous and more open. |
| Flower size and number. | Smaller and more numerous. | Larger and less numerous. |

What is claimed is:

1. A new and distinct cultivar of *Hesperantha* plant named 'MACHESPIBU', substantially as illustrated and described herein.

* * * * *